United States Patent [19]

Sexton

[11] Patent Number: 5,007,414
[45] Date of Patent: Apr. 16, 1991

[54] SPINE STRETCHER AND ALIGNER

[76] Inventor: Charles D. Sexton, 944 Waialae Cir., NE., Palm Bay, Fla. 32905

[21] Appl. No.: 387,729

[22] Filed: Aug. 1, 1989

[51] Int. Cl.⁵ ............................................. A61F 5/02
[52] U.S. Cl. ...................................... 128/78; 128/69
[58] Field of Search ................................ 128/69, 78

[56] References Cited

U.S. PATENT DOCUMENTS

| | | |
|---|---|---|
| 726,054 | 4/1903 | Hartford . |
| 726,055 | 4/1903 | Hartford .............................. 128/69 |
| 1,398,150 | 11/1921 | Pollard . |
| 1,833,426 | 1/1930 | Knudson ............................. 128/69 |
| 1,904,039 | 4/1933 | Bruder ................................. 128/69 |
| 1,934,918 | 11/1933 | Everson .................................. 27/1 |
| 2,159,654 | 5/1939 | Catlin ................................... 128/69 |
| 2,675,564 | 4/1954 | Hughes .................................... 5/82 |
| 2,777,440 | 1/1957 | Baker .................................. 128/69 |
| 3,362,402 | 1/1968 | Loeffel et al. ....................... 128/78 |
| 3,542,422 | 11/1970 | Flint ................................... 297/300 |
| 3,709,557 | 1/1973 | Light .................................. 297/230 |
| 3,813,148 | 5/1974 | Kraus ................................. 297/231 |
| 4,124,252 | 11/1978 | Safir .................................. 297/452 |
| 4,230,099 | 10/1980 | Richardson ........................ 128/69 |
| 4,245,628 | 1/1981 | Eichler ................................. 128/78 |
| 4,339,150 | 7/1982 | McNamara et al. ................ 297/284 |
| 4,471,993 | 9/1984 | Watson ............................... 297/230 |
| 4,506,929 | 3/1985 | Josefek .............................. 297/230 |
| 4,597,386 | 7/1986 | Goldstein ............................ 128/78 |
| 4,682,588 | 7/1987 | Curlee ................................. 128/70 |

Primary Examiner—V. Miller
Assistant Examiner—P. Kubel
Attorney, Agent, or Firm—John E. Benoit

[57] ABSTRACT

A spine stretcher and aligner comprising a rigid or semirigid base having two members mounted thereon, with each member having a sustantially flat face, with the faces opposing each other so as to form a channel therebetween. Each member has an arcuate configuration at the upper edge of the face, with the highest point of said edges being closer to one end of the channel than the other. The members are composed of a compressible material which permits movement of the material toward the center of the channel when the weight of the back presses downwardly on the members. Dowels may be removably inserted in the members so as to raise the height of the edges.

11 Claims, 3 Drawing Sheets

SPINE STRETCHER AND ALIGNER

This invention relates generally to a spine stretcher and aligner and more specifically to a portable spine stretcher and aligner which may be easily used by the individual desiring treatment.

BACKGROUND OF THE INVENTION

There are many known devices designed as back supports, and some devices designed as professional spinal corrective therapeutic tables and mechanisms. The present invention is not intended or designed to be a back support, nor is it designed for therapeutic use by professionals. The invention is intended and designed to provide a convenient home-use spinal column corrective device for individuals who suffer chronic or other back or neck ailments.

The goal of this invention is to create a safe, effective, practicable home-use device to provide immediate at-home relief from the pain eminent in most back disorders and to eventually correct such back disorders. The dislocation or pronation of a spinal part or member usually creates an area of pain, tension, and binding. This restricts spinal agility and impedes realignment of the displaced spinal member and related tissues.

To facilitate movement and realignment of a displaced spinal member, the tension and binding in the area must be reduced. Ample space for the member to move into must be created; also, the guiding and propelling forces necessary to move the problem member and related tissues back into their proper position and alignment must also be provided.

The present invention provides a tested proven device which provides all the requirements and surpasses the goals delineated above.

Firstly, this device is different from spinal process back support devices in that it is designed to cause the spinal column to stretch and relax at selected segments initially. The stretching and relaxing then progresses toward each end for the full length of the uniquely designed spinal process alignment channel. The curvature of this channel purposely deviates from the normal lordosis of the human spine and from the general lordotic curvature pattern common to back supports. The reason for the deviation is to induce exaggerated arching, stretching and spacing at bothersome segments of the spinal column as a person lies prone with his spinal column placed along the alignment channel. The increased arching of the back is induced by using a particular arcuate resilient means such as an extra firm compressible rubber, plastic foam, or polyethylene material to form cushioned channel walls which are higher and more convex than the curvature of the lumbar spinal section. In the preferred construction, cushions are formed by the material. The compressible material is firm and resilient, but not uncomfortable. The cushions form a convex channel wall edge which encourages and eventually causes one's tense suspended spinal column segments placed at the channel apex and nearby segments on either side of the extended convex curve apex to relax, stretch, and eventually come to rest on lower portions of the alignment channel only after spinal tissues have experienced substantial stretching and encouraged significant spacing between spinal parts. These spaces allow out-of-line parts to move into and fill the spaces provided by the spinal column stretching action. After that space has been provided, there is still the need for guiding and propelling forces which will serve to reposition the dislocated, problem-causing spinal member.

Secondly, the need for ample adjustable lateral forces to guide and propel the displaced member into its proper realignment position is also provided by the present device. The design of the convex channel causes one's own body weight to exert concentrated lateral force toward the center of the channel at the highest point of the arch. Further, these forces are provided simultaneously with the spinal stretching action described above. The intensity and direction of the lateral forces applied to the dislocated member are controllable by minute body movements, rolls or pressures against the side of the alignment channel provided through the full length of the arched surface. The major point of the lateral force concentration can also be controlled by the user either by pulling the cushions farther apart or by pressing them closer together while initially pressing one's weight upon the cushions.

Thirdly, the arched edges forming each side of the alignment channel are resilient members made of an extra firm rubber, plastic foam, or similar material, polymeric-coated and comfortable enough that one can fall asleep while both the stretch and lateral forces are working toward clearing up one's problem. Consequently, one may continue the corrective process as long and as often as he desires until realignment is completed or so long as he finds it further relieves his pain or condition. For chronic ailments, he can repeat the realignment action as necessary. Should the recommended use of this device aggravate rather than help the condition, instructions accompanying the device and one's own common sense judgment will tell him to discontinue use of the device and seek professional therapeutic treatment.

Lastly, although this device is most effective when one lies prone across it, the same device is usable and effective in numerous other positions or circumstances. Use of the device can help to relieve one's pain and promote spinal realignment while sitting and watching television, while sitting at a desk, or driving or riding in a vehicle. When the device is properly positioned and strapped snugly around one's body, jogging, walking or floor exercises actually enhance and speed up pain relief and corrective action in many instances. Also, use of this device is not limited to the lumbar, sacrum, cervical, or any other region. Its use is effective throughout the length of the spinal column. Further, when applied prudently to muscle pulls, spasms, pinched nerves, or painful problem areas located elsewhere around the body, the arched stretching and channel pressures of this device may sometimes give relief.

DETAILED DESCRIPTION OF THE INVENTION

Figure 1:
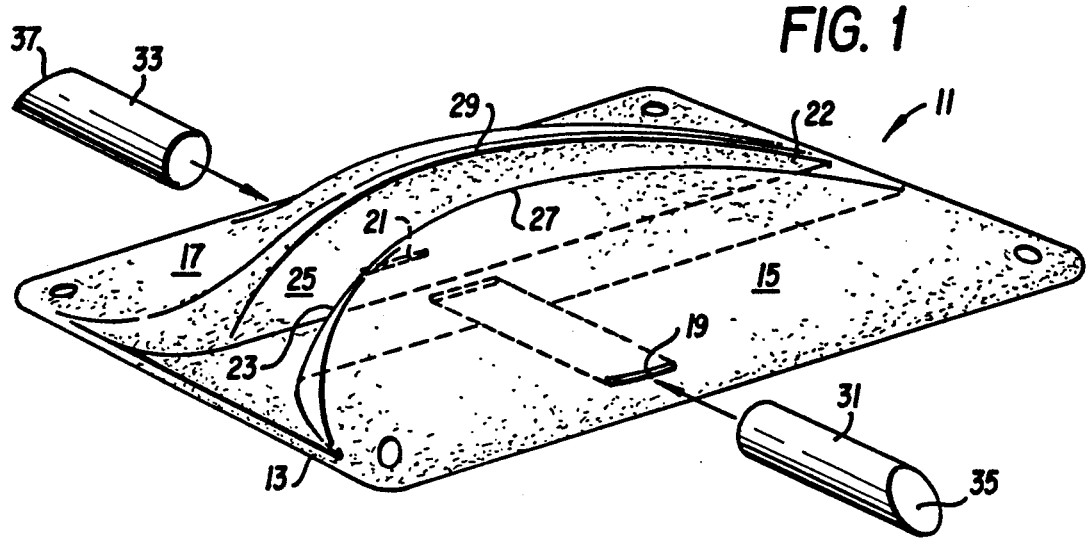
FIG. 1 is a perspective view of one embodiment of the present invention.
Figure 4:
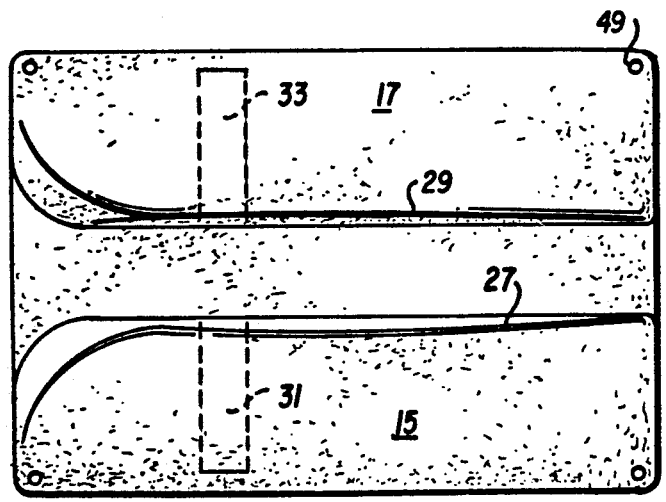
FIG. 4 is a top view of the device of FIG. 1.

FIG. 1 is a perspective view of spine stretcher and aligner 11 which includes a base 13 with resilient members such as cushions 15 and 17 extending above the base. In the embodiment of claim 1, the cushions are mounted on a rigid or semirigid base. Cushions 15 and 17 are comprised of a resilient material such as rubber or foam plastic of the extra firm variety for reasons which will become apparent as the discussion proceeds. Each of the cushions includes slots 19 and 21 which extend therethrough from the exterior of the pillow to channel 22, which is formed between walls 23 and 25 of cushions 15 and 17. Opposed walls 23 and 25 terminate at upper arcuate edges 27 and 29, which extend substantially the length of the cushions and base 13. Cushions 15 and 17 are configured such that the apex of edges 27 and 29 is nearest one end of the cushions. This provides the necessary curvature for the lower spinal area and the neck area, where the majority of the problems occur. Dowels 31 and 33 may be inserted into slots 19 and 21 for purposes which will be discussed as the description proceeds. When these dowels are in place, such as shown in FIG. 4, they have beveled ends 35 and 37 so as to substantially mate with the edge of the cushions.

Figure 3:
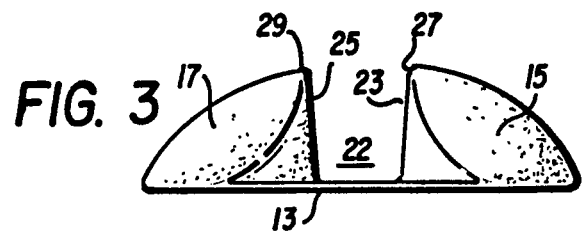
FIG. 3 is an end view of the device of FIG. 1.

As can be seen from FIG. 3, the outer surfaces of cushions 15 and 17 taper downwardly from edges 27 and 29 to the outer edges of base 13.

Figure 2:
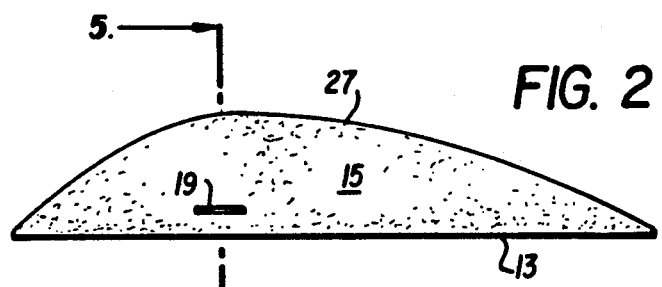
FIG. 2 is a side view of FIG. 1.

FIG. 2 more clearly indicates the curvature of edge 27, which has an apex nearer one end of cushion 15 than the other. Cushion 17 is configured substantially the same so as to provide channel 22. In the preferred embodiment, the channel is conformed so as to terminate in convex edges 27 and 29. This results in the channel being narrower at its ends than at a selected point along edges 27 and 29. This convexity is designed so that the width of the channel is greatest at the apex of edges 27 and 29. As previously indicated, this apex is preferably located approximately one-third of the distance from one end of the cushions. As an example, if the structure is mounted on a base approximately ten inches wide and fifteen inches long, each of the cushions would be approximately four inches wide, with top edges 27 and 29 forming an exaggerated lordotic-shaped curve with the apex being five inches from one end and ten inches from the other end. In this particular instance, when the cushions are placed at the edge of the base, inner edges 27 and 29 form channel 22 extending the distance of the base, with the channel being two inches at each end and two and one-half inches wide at the apex. As specifically constructed, this particular embodiment includes a channel which has zero depth at each end and a two and one-half inch depth at the apex of edges 27 and 29.

Figure 5:
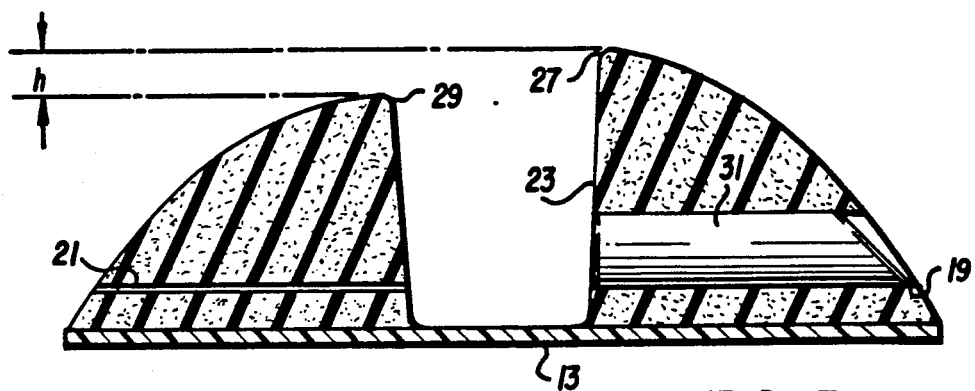
FIG. 5 is a sectional view taken through 5—5 of FIG. 2.

FIG. 5 illustrates the effect of inserting dowel 31 into slot 19 of cushion 15. While it is understood that both dowels would be used together, or neither would be used if not desired, FIG. 5 illustrates that the use of the dowel increases the height of edge 27 over that without the dowel, which is illustrated by edge 29. Slots 19 and 21 are located substantially directly below the apex of the associated edge of the cushion. These dowels may be used where cervical or other spinal areas require a more convex or higher arched lordotic surface. It is understood that any particular size of dowel may be used so as to provide varying adjustable heights.

As indicated in FIG. 4, holes 49 may be provided in base 13 so as to provide a means for placing a cord for carrying or hangup storage.

Figure 6:
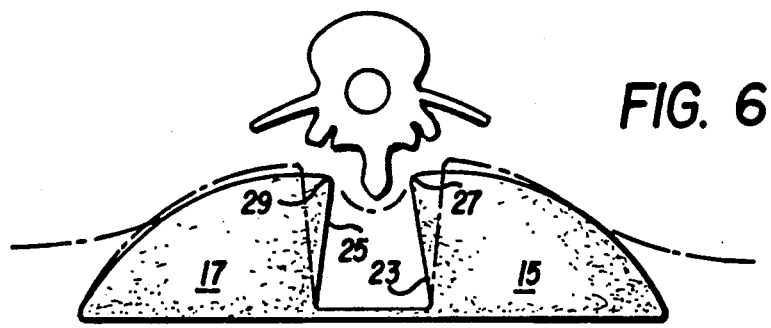
FIG. 6 is an end view of the device of FIG. 1 with a spinal column associated therewith.
Figure 7:
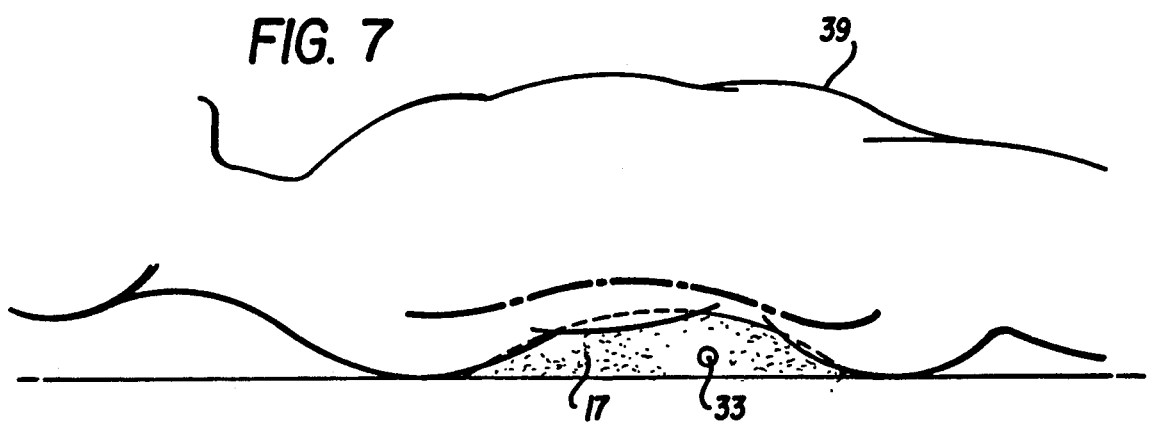
FIG. 7 is a side view of the device of FIG. 1 with the human body resting thereon.

FIG. 6 illustrates the device in use with an illustration of the cross-section of a spinal column resting over channel 22. This illustration shows how the downward pressure of the body itself causes movement of edges 27 and 29 in a direction away from their uncompressed position (shown in dotted lines) and toward each other, as shown by the solid lines. The concave configuration described above is required to keep the high points or apexes of the cushions from closing too much toward the center as one initially lowers his weight onto the device. The channel needs to remain open sufficiently to allow body pressure to build substantially before the channel narrows appreciably. The addition of one's torso weight onto the cushions, as shown in FIG. 7, strengthens the reaction pressure or force exerted by the cushions against dislocated spinal members which protrude and need realignment. Each cushion is tapered in convex arcs from the upper edge of the channel to the outer edge of the cushion, with the bulk of extra firm cushion material being nearest the channel.

The curvature of the cushion surfaces are designed to ensure that the cushions' reaction to one's body weight is to produce concentrated lateral force moments pushing any protrusions, where weight is greatest, toward the center of the alignment channel. This ensures pressure realignment of those spinal members nearest the center of the channel. Displaced members or tissue adjacent to the channel also experience some lateral energy forces until they move into proper alignment. Referring again to FIG. 6, the body weight rests mostly on the apex of edges 27 and 29, which moves the body parts in contact or near it towards the center of channel 22. As the body relaxes and exerts more weight onto the apex, the cushions exert increasing reactive force to realign dislocated spinal members and improve alignment of the spinous process, mammillary process, transverse process, and related nearby tissues. Progressively, the realignment continues away from the apex, up or down the spinal column toward each end of the channel. This is a gradual occurrence as relaxation sets in.

Figure 8:
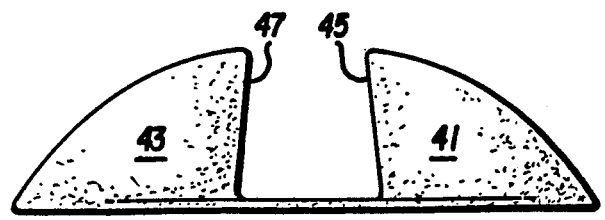
FIG. 8 is an end view of a modification of the device of FIG. 1.

FIG. 8 discloses a modification of the embodiment of claim 1 wherein cushions 41 and 43 have inclined walls 45 and 47, with the channel being narrower at the top than at the base. This results in increased lateral force on displaced members or tissue.

Figure 9:
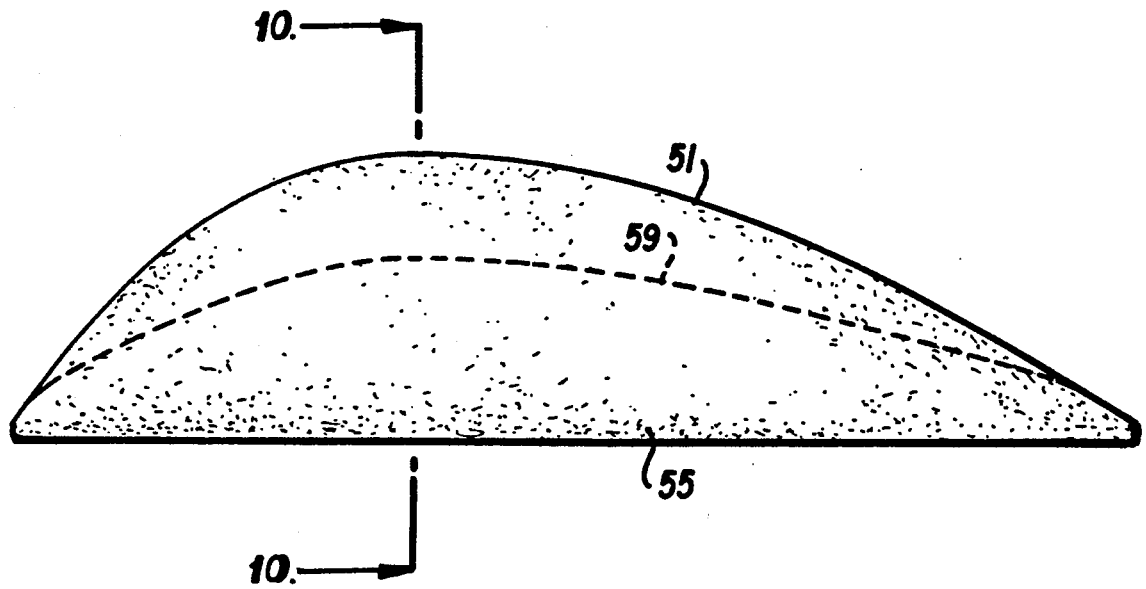
FIG. 9 is a side view of a modification of the embodiment of FIG. 1.
Figure 10:
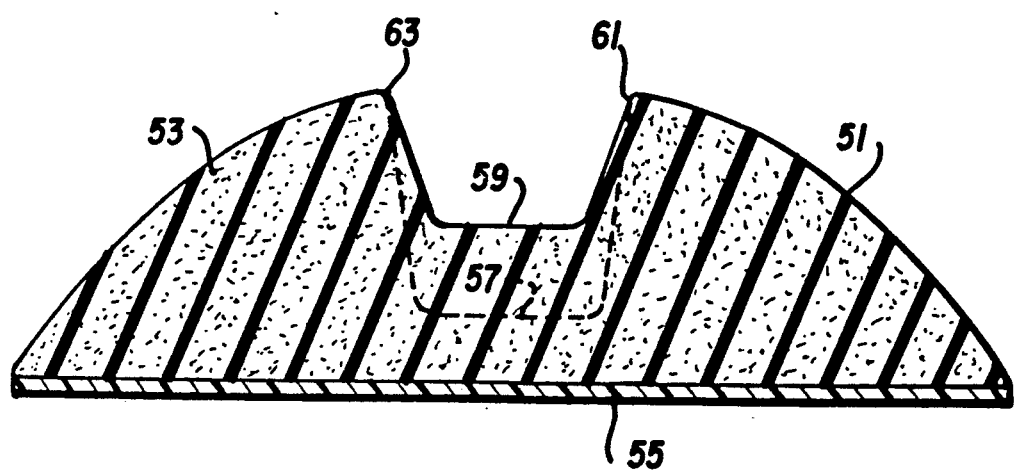
FIG. 10 is a sectional view taken along the lines 10—10 of FIG. 9.

FIGS. 9 and 10 show a further modification of the apparatus of FIG. 1. The resilient means 51 and 53 and base area 55 are molded as one piece from a material such as polyethylene. Channel 57 is not as deep since this construction requires a base having a greater depth. In this configuration, bottom 59 of channel 57 has an arcuate configuration with the apex of the bottom being substantially beneath the apex of curved edges 61 and 63. In this embodiment, it is preferred that the channel bottom be rounded. A spine stretcher and aligner such as shown in FIGS. 9 and 10 provides a device which is substantially lighter, which reduces shipping costs and makes it easy to carry.

The present invention has been tested and proven to be an effective means for individual treatment of back problems and specifically problems relating to stretching and alignment of the spinal column.

The above description and drawings are illustrative, only, since modifications could be made without departing from the invention. For instance, the arcuate resilient edges could be created by means other than cushions, such as resilient arcuate means carried by supports secured to the base. Accordingly, the scope of the invention is to be limited only by the following claims.

I claim:

1. A spine stretcher and aligner comprising a base;

a first resilient member extending above said base, said first member having a first arcuate upper edge extending substantially the length of said member and extending upwardly of said base;

a second resilient member extending above said base, said second member having a second arcuate upper edge opposed to and spaced from said first upper edge of said first member, said second arcuate upper edge having substantially the same configuration as said first arcuate upper edge;

said first and second arcuate upper edges having a curvature greater than the normal lordosis of the human spine;

said arcuate edges being configured such that the apex of said upper arcuate edges is nearest one end of said members.

2. The spine stretcher and aligner of claim 1 wherein each of said members slope downwardly from said upper arcuate edges outwardly toward said base.

3. The spine stretcher and aligner of claim 1 wherein said arcuate upper edges of said members are concave relative to each other.

4. The spine stretcher and aligner of claim 3 wherein the distance between said arcuate upper edges is greatest at the apex of said arcuate edges.

5. The spine stretcher and aligner of claim 4 wherein the distance between said arcuate upper edges is substantially two inches at either end of said edges and substantially two and one-half inches at the apex of said edges.

6. The spine stretcher and aligner of claim 1 further comprising means for raising the height of the apex of said arcuate upper edges of said members.

7. The spine stretcher and aligner of claim 6 wherein said resilient members comprise cushions and the means for raising the height of the apex of said edges comprises slots in each of said cushions below said apex; and dowels removably inserted into said slots.

8. The spine stretcher and aligner of claim 7 wherein said cushions form a channel and said channel is wider at its base than at said upper edges.

9. The spine stretcher and aligner of claim 8 wherein said cushions are comprised of rubber.

10. The spine stretcher and aligner of claim 8 wherein said cushions are comprised of foam plastic.

11. The spine stretcher and aligner of claim 1 wherein said base and said resilient members are molded as a single plastic element.

* * * * *